United States Patent [19]

Schaus et al.

[11] Patent Number: 4,698,347

[45] Date of Patent: Oct. 6, 1987

[54] OCTAHYDRO-OXAZOLO[4,5-G]QUINO-LINES DERIVATIVES AND DECAHYDRO QUINOLINE INTERMEDIATES AND THEIR USE AS DOPAMINE D-2 AGONISTS

[75] Inventors: John M. Schaus; Robert D. Titus, both of Indianapolis, Ind.

[73] Assignee: Eli Lilly and Company, Indianapolis, Ind.

[21] Appl. No.: 939,932

[22] Filed: Dec. 11, 1986

Related U.S. Application Data

[60] Division of Ser. No. 743,198, Jun. 10, 1985, Pat. No. 4,659,832, which is a continuation-in-part of Ser. No. 637,232, Aug. 2, 1984, abandoned.

[51] Int. Cl.[4] .................... A61K 31/41; C07D 498/04; C07D 215/20
[52] U.S. Cl. ..................................... 514/293; 546/83; 546/164
[58] Field of Search .................. 546/83, 164; 514/293

[56] References Cited

U.S. PATENT DOCUMENTS 4,230,861 10/1980 Kornfeld et al. ..................... 546/82

OTHER PUBLICATIONS

March, *Advanced Organic Chemistry*, 2nd Ed., 1977, pp. 381–383, 477–478, 1127, 658–659.
Newkome and Puadler, *Contemporary Heterocyclic Chemistry*, (1982), pp. 37–38.
*Organic Reactions* (Eds. Roger Adams et al.), vol. 10, p. 148.

*Primary Examiner*—Henry R. Jiles
*Assistant Examiner*—J. Richter
*Attorney, Agent, or Firm*—Charles W. Ashbrook; Leroy Whitaker

[57] ABSTRACT

Trans-(±)-2- and/or -5-permissibly substituted octahydro-oxazolo[4,5-g]quinolines, acid addition salts thereof and individual enantiomers thereof, useful as dopamine agonists or intermediates of the preparation of dopamine agonists.

37 Claims, No Drawings

OCTAHYDRO-OXAZOLO[4,5-G]QUINOLINES DERIVATIVES AND DECAHYDRO QUINOLINE INTERMEDIATES AND THEIR USE AS DOPAMINE D-2 AGONISTS

This application is a division of application Ser. No. 743,198, filed June 10, 1985, now U.S. Pat. No. 4,659,832, which is a continuation-in-part of application Ser. No. 637,232, filed Aug. 2, 1984, now abandoned.

SUMMARY OF THE INVENTION

This invention provides trans-(±)-2,5-permissibly-substituted-4,4a,5,6,7,8,8a,9-octahydro-oxazolo[4,5-g]quinolines of the structure

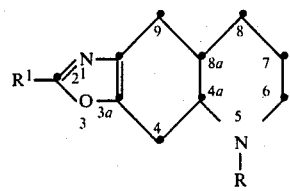

wherein R is H, benzyl, methyl, ethyl, allyl or n-propyl, $R^1$ is Cl, Br, H, $C_1$-$C_3$ alkyl, O—$C_1$-$C_3$ alkyl, OH, $NH_2$, $NHC_{1-3}$ straight chain alkyl, $N(C_{1-3}$ straight chain alkyl$)_2$, 1-pyrrolidinyl, 1-piperidinyl or $NHCOC_{1-3}$alkyl, and pharmaceutically-acceptable acid addition salts thereof. When $R^1$ is $N(C_{1-3}$ straight chain alkyl$)_2$, the two alkyl groups are not necessarily identical.

While the compounds represented by I except when R is H or benzyl and $R^1$ is other than OH, Cl or Br, are active drugs; i.e., dopamine agonists, several are also useful intermediates; for example, compounds in which $R^1$ is $NH_2$ can be acylated to yield compounds in which $R^1$ is $NHCOC_{1-3}$ alkyl. Compounds in which R is H are also intermediates in that they can, in general, be alkylated to yield derivatives in which R is methyl, ethyl, allyl or n-propyl. Compounds in which R is alkyl can be dealkylated by treatment with CNBr followed by hydrolysis to yield compounds in which R is H. In compounds in which R is benzyl, the benzyl group can be removed by hydrogenolysis. Compounds in which $R^1$ is O—$C_{1-3}$ alkyl can be dealkylated to yield compounds in which $R^1$ is OH.

As previously stated, compounds according to I except where R is H or benzyl, and $R^1$ is other than OH, Cl or Br are dopamine D-2 agonists, manifesting their activities in tests designed to demonstrate utility as prolactin secretion inhibitors, in the treatment of Parkinson's disease, in treating sexual dysfunction, anxiety or depression or as hypotensive agents.

In the above formula, the term "$C_{1-3}$ alkyl" includes methyl, ethyl, n-propyl and isopropyl while the term "straight-chain $C_{1-3}$ alkyl" includes only the first three radicals.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydroiodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to I above have two asymmetric carbons (optical centers) at 4a and 8a and can thus exist as four stereoisomers occurring as two racemic pairs, ordinarily designated as the trans-(±) racemate and the cis-(±) racemate. The trans-(±) racemates (I) of this invention are composed of a trans-(−)-4aR,8aR stereoisomer represented by III below and a trans-(+)-4aS,8aS stereoisomer represented by IIIa

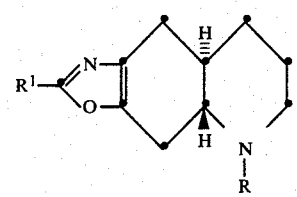

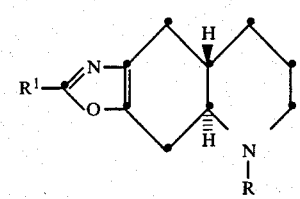

wherein R and $R^1$ have their previously assigned meanings. The trans-(−)-4aR,8aR stereoisomers represented by III, wherein R is other than H or benzyl and $R^1$ is other than OH, Cl or Br, constitute the active dopamine D-2 agonist component of the racemate (I) and are preferred over the trans-(+)-stereoisomers (IIIa).

The trans-(−)-4aR,8aR enantiomers according to III thus form a second and preferred aspect of this invention.

As dopamine D-2 agonists, compounds represented by III above in which R is other than H or benzyl and $R^1$ is other than Cl, Br or OH may be employed for use as drugs either as the free base or as a pharmaceutically-acceptable acid addition salt thereof.

Preferred groups of drugs according to III are those in which (1) R is n-propyl
(2) $R^1$ is $NH_2$
(3) $R^1$ is $NHCH_3$
(4) $R^1$ is $N(CH_3)_2$
(5) $R^1$ is NH—CO—$CH_3$ Compounds of this invention include, illustratively, Trans-(±)-2-amino-5-ethyl-4,4a,5,6,7,8,8a,9-octahydro-oxazolo[4,5-g]quinoline maleate, Trans-(±)-2-n-propylamino-5-n-propyl-4,4a,5,6,7,8,8a,9-octahydro-oxazolo[4,5-g]quinoline sulfate, Trans-(±)-5-ethyl-4,4a,5,6,7,8,8a,9-octahydrooxazolo[4,5-g]quinoline,
Trans-(±)-2-dimethylamino-5-n-propyl-4,4a,5,6,7,8,8a,9-octahydro-oxazolo[4,5-g]quinoline dihydrobromide,
4aR,8aR-2-methylethylamino-5-ethyl-4,4a,5,6,7,8,8a,9-octahydro-oxazolo[4,5-g]quinoline succinate,
4aS,8aS-2-amino-5-methyl-4,4a,5,6,7,8,8a,9-octahydro-oxazolo[4,5-g]quinoline dihydrochloride,
Trans-(±)-2-methylamino-5-n-propyl-4,4a,5,6,7,8,8a,9-octahydro-oxazolo[4,5-g]quinoline tartrate,
4aR,8aR-2-dimethylamino-5-ethyl-4,4a,5,6,7,8,8a,9-octahydro-oxazolo[4,5-g]quinoline phosphate,
4aR,8aR-2-acetylamino-5-methyl-4,4a,5,6,7,8,8a,9-octahydro-oxazolo[4,5-g]quinoline terephthalate,
trans-(±)-2-propionylamino-5-ethyl-4,4a,5,6,7,8,8a,9-octahydro-oxazolo[4,5-g]quinoline dinitrobenzoate,
Trans-(±)-2-amino-5-n-propyl-4,4a,5,6,7,8,8a,9-octahydro-oxazolo[4,5-g]quinoline methanesulfonate (mesylate),
Trans-(±)-2-dimethylamino-5-n-propyl-4,4a,5,6,7,8,,8a,9-octahydro-oxazolo[4,5-g]quinoline p-toluene sulfonate (p-tosylate) and the like.

Compounds represented by Formula III wherein R is $C_{1-3}$ straight chain alkyl or allyl, as dopamine (D-2) agonists are substantially devoid of other agonist or antagonist (blocking) activities. As dopamine D-2 agonists, the compounds are useful in treating Parkinson's Syndrome, in treating sexual dysfunction, as antidepressants or as anti-anxiety agents, in lowering blood pressure in hypertensive mammals and in inhibiting prolactin secretion. Thus, other embodiments of this invention include the treatment, by the racemates (I) or the 4aR,8aR-(III) enantiomers wherein R is other than H or benzyl, and $R^1$ is other than OH, Cl or Br of hypertension, of depression, of anxiety, of Parkinson's disease, of sexual dysfunction, and of disease states characterized by an excess of prolactin secretion such as galactorrhea and inappropriate lactation.

A still further embodiment of this invention is the provision of pharmaceutical formulations for administering drugs according to I or III wherein R is other than H or benzyl and $R^1$ is limited as above in the treatment methods outlined above.

The trans-(±)-racemates represented by I can be used as D-2 agonists, and also as a source of the 4aR,8aR-enantiomers.

Racemic compounds of this invention where, in Formula I, $R^1$ is $R^3$ and $R^3$ is $NH_2$, $NH(C_{1-3}$ alkyl), or $N(C_{1-3}$ alkyl$)_2$, and $R^4$ is other than allyl, are readily synthesized according to the following reaction scheme:

Synthetic Route 1

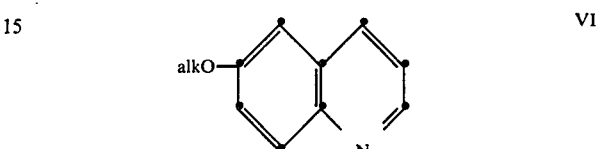

IV V wherein $R^4$ is methyl, ethyl or n-propyl, $R^3$ is as previously defined and the 4a,8a ring fusion is trans. Formula IV above represents an iso-urea, tautomeric with the corresponding urea is represented by the following equilibrum

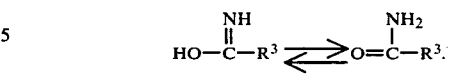

The other starting material (V) for Synthetic Route I is prepared by brominating an N—$C_{1-3}$ straight-chain alkyl-6-oxodecahydroquinoline. These latter compounds can be prepared by quaternizing a 6-alkoxyquinoline of formula VI

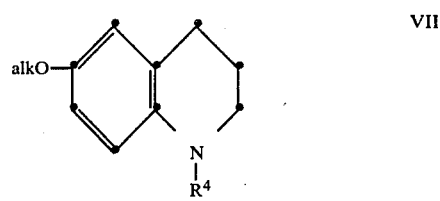

wherein alk is lower alkyl, with a $C_{1-3}$ straight-chain alkyl halide ($R^4X$) and the quaternized salt hydrogenated to yield an N—$C_{1-3}$ straight-chain alkyl-6-alkoxy-1,2,3,4-tetrahydroquinoline of formula VII

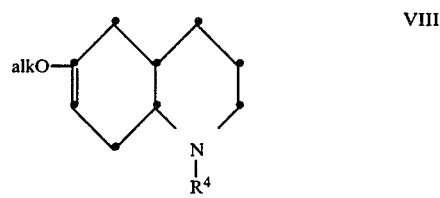

wherein $R^4$ is $C_{1-3}$ straight-chain alkyl. The particular $C_{1-3}$ alkyl group ($R^4$) remains intact through the next two reduction steps: a Birch reduction followed by a sodium cyanoborohydride (or sodium borohydride) reduction to yield, ultimately, an octahydroquinoline of the formula VIII

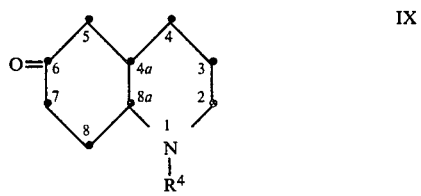

wherein $R^4$ is $C_{1-3}$ straight-chain alkyl, alk has its previous meaning, and the ring junction hydrogens are trans. This enol ether, upon treatment with acid, yields the N-substituted decahydroquinolin-6-one (IX)

IX in which the 4a,8a ring junction is trans-fused and the N-substituent ($R^4$) is $C_{1-3}$ straight-chain alkyl. The above procedure is set forth in greater detail in Schaus Ser. No. 384,817 filed June 3, 1982, now abandoned and in a CIP, Ser. No. 521,863 filed Aug. 10, 1983, allowed Mar. 21, 1985 and now U.S. Pat. No. 4,540,787.

Bromination of IX at C-7 using, for example, hydrogen bromide and bromine in glacial acetic acid, permissibly in the presence of UV light, yields V, one starting material for use in Synthetic Route I. This procedure is more fully described in the copending application of Titus and Kornfeld, Ser. No. 604,687 filed 4-27-84 and now U.S. Pat. No. 4,537,893.

An alternate preparation of the trans-($\pm$)-1-$C_{1-3}$ straight-chain alkyl-6-oxodecahydroquinoline (IX) is disclosed in U.S. Pat. No. 4,198,415 Cols. 4–5 (where it is compound number VII in the Reaction Scheme).

The optically-active octahydro-oxazolo[4,5-g]quinolines of formulas III and IIIa can be prepared by resolution of the trans-($\pm$) racemates represented by I above. A preferred procedure, however, is to resolve the trans-($\pm$) ketone (IX) using the procedure of Schaus and Booher, Ser. No. 439,107 filed Nov. 1, 1982, now U.S. Pat. No. 4,471,121 issued Sept. 11, 1984 whereby the racemic ketone is resolved via an optically-active ditoluoyltartaric acid salt. The 4aR,8aR enantiomer thus prepared, IXa,

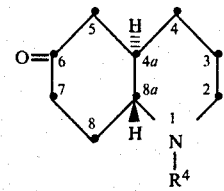

wherein $R^4$ has its previous meaning, can then be substituted for the racemic ketone IX in Synthetic Route I; i.e., bromination of IXa yields a 4aR,8aR-1-$C_{1-3}$ straight-chain alkyl-6-oxo-7-bromodecahydroquinoline (Va—V in which the bridgehead hydrogens are 4aR,8aR) which derivative then reacts with a urea or a tautomeric iso-urea (IV) to yield compounds according to III in which $R^1$ is $R^3$, and R is $R^4$, a $C_1$-$C_3$ straight-chain alkyl group.

Those drugs of this invention in which $R^1$ is NH(CO—$C_{1-3}$ alkyl) in I, III or IIIa are prepared by acylating the corresponding compound in which $R^1$ is $NH_2$.

Compounds according to I, III or IIIa in which $R^1$ is H, O$C_{1-3}$ alkyl or $C_{1-3}$ alkyl are prepared according to Synthetic Route 2 below.

Synthetic Route 2

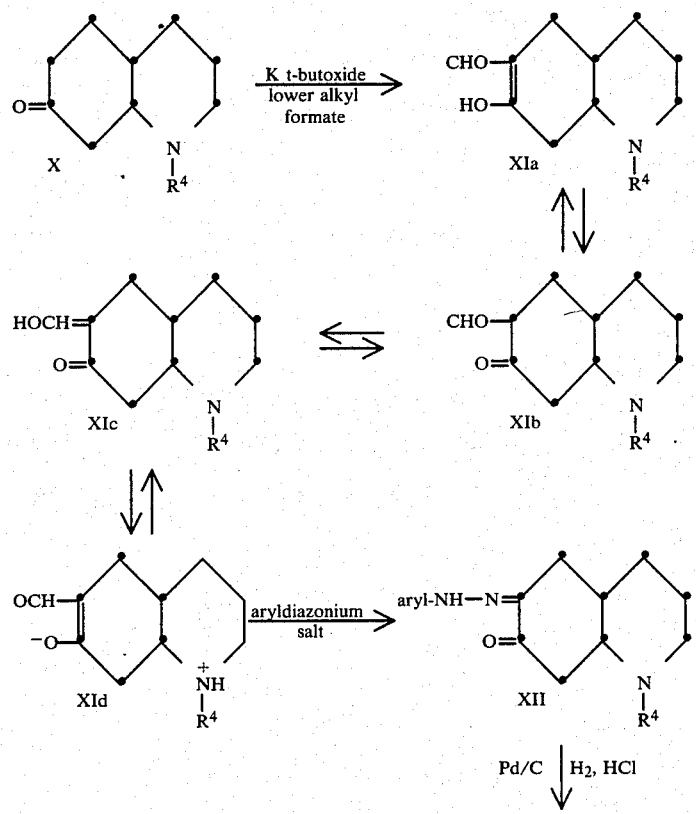

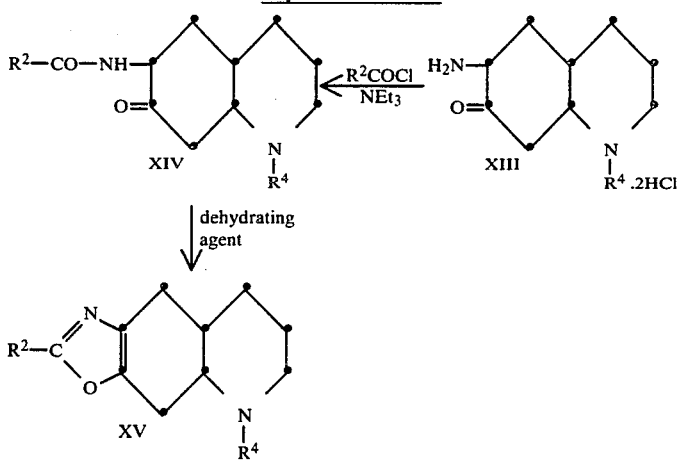

wherein $R^2$ is $C_{1-3}$ alkyl, O—$C_{1-3}$ alkyl or H and $R^4$ is $C_{1-3}$ straight chain alkyl or allyl.

In the above Synthetic Route 2, an isomeric (to IX) bicyclic ketone, a trans-($\pm$)-1-$C_{1-3}$ straight chain alkyl-7-oxodecahydroquinoline, is reacted with a lower alkyl formate such as ethyl formate, in the presence of base—K t-butoxide, NaH or the like—in THF or other suitable solvent, to yield a 6-formyl-7-oxo derivative represented by four tautomeric structures, XIa–d. This reaction yields exclusively the 6-formyl derivative rather than a mixture of 6-formyl and 8-formyl derivatives as might be expected. (see Schaus, Ser. No. 438,834, filed 11-3-82, now abandoned, refiled as a continuation-in-part Ser. No. 636,959, now U.S. Pat. No. 4,567,266 filed July 31, 1984 for a more detailed description of this formylation procedure). Reaction of the 6-formyl derivative (the tautomers XIa–d) with an aryldiazonium salt such as phenyldiazonium bromide, p-methoxyphenyldiazonium sulfate, naphthalenediazonium chloride, p-nitrophenyldiazonium chloride, phenyldiazonium chloride or the like via a Japp-Klingemann Reaction—see *Ann.*, 247 190 (1888); *Ber.*, 20, 2942, 3284, 3398 (1887); *Org. Reactions*, 10, 143 (1959)—results in the formation of a 6-arylhydrazone (XII) with concomitant loss of the formyl group. Hydrogenation of the 6-arylhydrazone in acidic ethanol with a noble metal catalyst, supported or unsupported, such as 5% Pd/C at high pressure, yields a 1-alkyl-6-amino-7-oxodecahydroquinoline (XIII) in the form of an acid addition salt, conveniently a dihydrochloride salt. The diamine (XIII) forms acid addition salts with the same acids listed above for the octahydro-oxazolo[4,5-g]quinolines (I, III and IIIa). Acylation of the primary amine (XIV) followed by a ring closure reaction with a dehydrating agent such as $POCl_3$ yields those compounds according to I above in which R is $R^4$ and $R^4$ is $C_{1-3}$ straight chain alkyl and $R^1$ is $R^2$ and $R^2$ is H, $OC_{1-3}$ alkyl or $C_{1-3}$ alkyl. Treatment of an intermediate wherein $R^2$ is $OC_{1-3}$alkyl with acid in a mutual solvent; i.e. aqueous HCl, cleaves the alkyl group to a hydroxy isomeric with a ketone. Structures XXI and XXIa illustrate this isomerism.

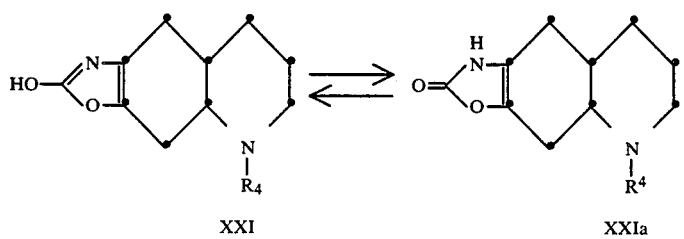

XXI    XXIa wherein $R^4$ is methyl, ethyl, n-propyl or allyl. Compounds according to XXI are named as trans-($\pm$) 2-hydroxy-5-substituted 4,4a,5,6,7,8,8a,9-octahydro-oxazolo[4,5-g]quinolines and those according to XXIa are trans-($\pm$)-5-substituted-4,4a,5,6,7,8,8a,9-octahydro-oxazolo[4,5-g]quinolin-2(1H)-ones.

In Synthetic Route 2 above, if an optically active enantiomer is employed; i.e., 4aR,8aR-1-$C_{1-3}$ alkyl-7-oxodecahydroquinoline, the final product will be the optically active octahydro-oxazolo[4,5-g]quinoline, III or IIIa, in which $R^1$ is $R^2$ and R is $R^4$ (XVI and XVIa below)

XVI

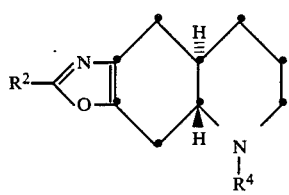

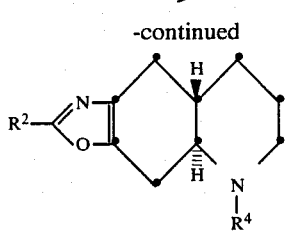

Those compounds according to I, III or IIIa wherein $R^1$ is OH are prepared by ether cleavage or hydrolysis of the corresponding compound wherein $R^1$ is O—$C_{1-3}$ alkyl.

Those compounds according to I, III or IIIa in which $R^1$ is 1-pyrrolidinyl or 1-piperidinyl are prepared by reacting the corresponding 2-O($C_{1-3}$ alkyl), 2-bromo or 2-chloro compound with the appropriate secondary amine. These latter halo derivatives are prepared by halogenating compounds in which $R^1$ is OH.

Finally, compounds according to I, III or IIIa in which R is allyl particularly where $R^1$ is $NH_2$ can be prepared from 6-oxo or 7-oxodecahydroquinoline (X) according to Synthetic Route 3 below.

Synthetic Route 3

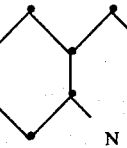

where one of X and Y represents oxygen and the other represents two hydrogens, and $R^6$ is $C_{1-3}$ alkyl or benzyl. In the above procedure, the $R^6$ group is replaced by a cyano group on reaction with CNBr in a mutual inert solvent. The cyano group is then removed by hydrolysis to yield a secondary amine which can be allylated by standard procedures. The N-allyl product when X is O and Y is $H_2$ (XX) can be brominated to yield V in which R is allyl in Synthetic Route I, being careful not to brominate the N-allyl group in producing this compound. Should bromination occur despite precautions to avoid it, an alternate route can be used in which a compound according to XVII wherein $R^6$ is benzyl and the 6-oxo group (X is O, Y is $H_2$) is protected as by ketal formation, can be hydrogenated so as to hydrogenolyze the benzyl group to form a secondary amine. Removal of the ketal protecting group with acid yields XIX where X=O and Y=$H_2$ which compound can be allylated to give XX. The above procedures are outlined in the copending application of Titus and Bach, Ser. No. 535,522 filed 9-26-83 and now abandoned.

When Y is O and X is $H_2$, the 1-allyl-7-oxodecahydroquinoline can be used as the starting material (X) in Synthetic Route 2.

A second synthetic procedure is available for preparing compounds according to I, III or IIIa in which $R^1$ is $NHC_{1-3}$alkyl or $N(C_{1-3}alkyl)_2$. This procedure involves reacting I ($R^1$=O—$C_{1-3}$ alkyl), or an enantiomer thereof, with a primary or secondary amine $H_2N$—$C_{1-3}$alkyl or $HN(C_{1-3}alkyl)_2$, under pressure.

In any of the above synthetic procedures, the optically-active enantiomer, the 4aR,8aR-6-oxodecahydroquinoline, 4aS,8aS-6-oxodecahydroquinoline (Synthetic Route 1-ultimate starting material IX) or 4aR,8aR-7-oxodecahydroquinoline or 4aS,8aS-7-oxodecahydroquinoline (Synthetic Route 2-X) can be used in place of the trans-(±) racemate actually represented to yield optically active final products III or IIIa.

This invention is further illustrated by the following specific examples. In the examples, the term "flash chromatography" refers to the chromatographic procedure described by Still et al., *J. Org. Chem.*, 43, 2923 (1978).

EXAMPLE 1

Preparation of Trans-(±)-2-amino-5-n-propyl-4,4a,5,6,7,8,8a,9-octahydro-oxazolo[4,5-g]quinoline A solution was prepared by dissolving 1.95 g. of trans-(±)-1-n-propyl-6-oxodecahydroquinoline in 25 ml. of glacial acetic acid. Two and three tenths milliliters of 37% (by weight) hydrogen bromide in glacial acetic acid were added followed by the dropwise addition of 0.6 ml. of bromine dissolved in 5 ml. of glacial acetic acid. The reaction mixture was stirred for one-half hour after all the reactants had been added. Volatile constituents were then removed in vacuo yielding, as a residue, trans-(±)-1-n-propyl-6-oxo-7-bromodecahydroquinoline hydrobromide. Ten millimoles of this salt were dissolved in 10 ml. of methanol. One and two-tenths grams of urea were added thereto. The resulting mixture was refluxed for about 24 hours under a nitrogen blanket. The reaction mixture was cooled to about room temperature, and the solvent removed in vacuo. The residue was dissolved in water, and the aqueous solution made basic by the addition of 14N aqueous ammonium hydroxide. The alkaline layer was extracted several times with an equal volume of methylene dichloride. The organic extracts were combined, and the combined extracts washed with saturated aqueous sodium chloride and ten dried. Removal of the solvent in vacuo yielded a brown viscous oil comprising trans-(±)-2-amino-5-n-propyl-4,4a,5,6,7,8,8a,9-octahydro-oxazolo[4,5-g]quinoline formed in the above reaction. The residue was dissolved in chloroform containing 5% methanol and a trace of ammonium hydroxide and chromatographed over silica gel (eluant was $CHCl_3$ containing 5% methanol and a trace of ammonium hydroxide). Fractions containing the desired oxazoloquinoline were combined to yield, after evaporation of the solvent, a yellow viscous oil which slowly crystallized. The crystalline solid, trans-(±)-2-amino-5-n-propyl-4,4a,5,6,7,8,8a,9-octahydro-oxazolo[4,5-g]quinoline, was dissolved in methanol and the methanolic solution saturated with gaseous HCl. The solvent was removed and the residue recrystallized from ethanol. Two-tenths grams of trans-(±)-2-amino-5-n-propyl-4,4a,5,6,7,8,8a,9-octahydro-oxazolo[4,5-g]quinoline dihydrochloride were obtained melting above 225° C.; molecular ion at 235 by mass spectrum.

Analysis: Calc.; C, 50.65; H, 7.52; N, 13.63; C, 50.52; H, 7.28; N, 13.34.

The above procedure can be repeated using a 4aR,-8aR-1-substituted-6-oxodecahydroquinoline as the starting material. (The synthesis of 1-n-propyl-6-oxodecahydroquinoline is disclosed in Preparation I below). Three and nine tenths grams of 4aR,8aR-1-n-propyl-6-oxodecahydroquinoline were dissolved in 40 ml of glacial acetic acid. Four and six tenths ml of 31% HBr in glacial acetic acid were added followed by the dropwise addition of a solution of 1.2 ml of Br$_2$ in 10 ml of glacial acetic acid. After stirring at room temperature for about 0.5 hr., the solvent was removed in vacuo, leaving as a residue, an orange foam comprising (−)-1-n-propyl-6-oxo-7-bromodecahydroquinoline formed in the above reaction. The orange foam was dissolved in 30 ml of methanol. 1.32 g of urea were added and the mixture heated to reflux temperature for about 18 hours, at which time it was poured over ice. The acidic aqueous mixture was made basic with 14N aqueous ammonium hydroxide, and the basic solution extracted several times with equal volumes of methylene dichloride. 4aR,8aR-2-amino-5-n-propyl-4,4a,5,6,7,7,8a,9-octahydro-oxazolo[4,5-g]quinoline formed in the above reaction being insoluble in aqueous base, passed into the organic layer. The organic layers were combined; the combined layers were washed with water and with brine and were then dried. Evaporation of the solvent left a dark viscous residue. The residue was flash chromatographed over silica, using methylene dichloride containing 3% methanol and a trace of 14N aqueous ammonium hydroxide as the eluant. Fractions containing the desired material as shown by TLC 9:1 CH$_2$Cl$_2$/MeOH+Tr.NH$_4$OH were combined and the solvent removed in vacuo. The residual pale yellow foam, comprising purified 4aR,8aR-2-amino-5-n-propyl-4,4a,5,6,7,8,8a,9-octahydro-oxazolo[4,5-g]quinoline was dissolved in MeOH and the resulting solution saturated with gaseous HCl. The hydrochloride salt thus formed was recrystallized from a methanol/ethyl acetate solvent mixture; yield=0.25 g (from 3.9 g of starting ketone). The salt had the following physical characteristics:

M.P.=above 225° C.
Mass spectrum: m/e at 235.
$[\alpha]_D^{20}=103.1°$ (H$_2$O, c=1.0).
Analysis: Calc.: C, 50.65; H, 7.52; N, 13.63; C, 50.93; H, 7.25; N, 13.39.

The above procedure was repeated starting with 4aS,8aS-1-n-propyl-6-oxodecahydroquinoline to prepare 4aS,8aS-2-amino-5-n-propyl-4,4a,5,6,7,8,8a,9-octahydro-oxazolo[4,5-g]quinoline, purified as the hydrochloride salt; yield =0.26 g (from 3.9 g of starting ketone);

M.P.=above 225° C.; molcular ion at 235;
$[\alpha]_D^{20}=102.0°$ (H$_2$O, c=1.0).
Analysis: Calc.; C, 50.65; H, 7.52; N, 13.63; Found: C, 50.37; H, 7.70; N, 13.69.

EXAMPLE 2

Preparation of
Trans-(±)-2-methyl-5-n-propyl-4,4a,5,6,7,8,8a,9-octahydro-oxazolo[4,5-g]quinoline A solution was prepared by dissolving 9.9 g. of lithium in 2 l. of anhydrous liquid ammonia. 98.7 g. of 4-(3-n-propylamino)propylanisole were dissolved in a mixture of 27.8 ml. of anhydrous ethanol and 300 ml. of THF. This solution was added slowly in dropwise fashion with stirring to the lithium in liquid ammonia solution. After the addition had been completed, the reaction mixture was stirred for about 45 minutes. Water was then added slowly until the blue color of dissolved Li had been discharged. A stream of warm N$_2$ was passed over the reaction mixture overnight to evaporate the ammonia. Additional water was then added to dissolve the salts which had formed. The alkaline aqueous solution was extracted three times with equal volumes of diethyl ether. The ethereal extracts were combined and dried. Evaporation of the ether yielded 93.2 g. of solvated 1-methoxy-4-(3-n-propylamino)propyl-1,4-cyclohexadiene; yield=93.5%.

One hundred twenty-one grams of 1-methoxy-4-(3-n-propylamino)propyl-1,4-cyclohexadiene were dissolved in 1 l. of 15% aqueous sulfuric acid. The acidic solution was refluxed for about 6 hours and was then poured over ice. The dilute acidic solution was made basic with 50% aqueous sodium hydroxide. The now-basic aqueous solution was extracted with methylene dichloride. The methylene dichloride extract was dried and the solvent removed therefrom to yield 25.6 g of cis-(±)-1-n-propyl-7-oxodecahydroquinoline.

About 23.8 g of the above crude product were dissolved in 300 ml. of methanol to which solution was added 1.3 g. of sodium methylate. The reaction mixture was stirred overnight at room temperature, and was then diluted with water. The aqueous mixture was made strongly basic and the basic mixture extracted with methylene dichloride. The methylene dichloride extract was dried, and the solvent removed therefrom to yield 11.4 g of trans-(±)-1-n-propyl-7-oxodecahydroquinoline.

The compound had the following physical characteristics:

IR(CHCl$_3$) 2904, 1457, 1081 cm$^{-1}$.

Proton NMR (CDCl$_3$, 270 MHz, δ): 2.94 (bd, 1H, J=2.0; 2.79 (bd, 1H, J=2.5); 2.61-2.50 (m, 1H); 2.42-1.98 (m, 6H), 1.92-1.22 (m, 8H); 1.10-0.98 (m, 1H); 0.82 (t, 3H, J=1.2).

A solution was prepared by dissolving 19.5 g. of trans-(±)-1-n-propyl-7-oxodecahydroquinoline and 32.3 ml. of ethyl formate in 100 ml. of THF. This solution was in turn added to a solution of 22.4 g. of potassium t-butoxide in 400 ml. of THF at 0° C. This reaction mixture was stirred for about 1 hour at which time TLC (THF plus a trace of ammonium hydroxide) indicated an absence of starting material. Next a solution of benzene diazonium chloride was prepared by dissolving 9.3 g. of aniline in 60 ml. of 1:1 12N hydrochloric acid/water mixture. This solution was cooled rapidly by the addition of ice. A solution of 6.8 g. of sodium nitrite and 30 ml. of water was then added while maintaining the temperature of the reaction at about 0° C. by the addition of ice.

The pH of the reaction mixture containing the formylated ketone was adjusted to pH=about 6 by the addition of 10% hydrochloric acid. A solution of 42.4 g. of sodium acetate in 100 ml. of water was added, followed by the addition of the benzene diazonium chloride solution prepared above. This new reaction mixture was stirred overnight at about 4° C. An orange solid formed which was separated by filtration; wt=12.9 g. The solid was discarded.

The filtrate was made strongly basic with 15N aqueous ammonium hydroxide. The resulting two phase system was extracted several times with equal volume of 3:1 chloroform/isopropanol solvent mixture. The organic extracts were combined and the solvent evaporated therefrom in vacuo to yield 10.5 g. of a red viscous residue. This residue was dissolved in methylene dichloride containing 5% methanol and a trace of ammonium hydroxide and the solution flash chromatographed over silica. The column was developed and the products eluted with the same solvent mixture. Fractions shown by TLC (9:1 methylene dichloride/methanol plus a trace of ammonium hydroxide) to contain the desired product were combined, and the solvent evaporated therefrom to yield 9.4 g. of a bright orange solid comprising trans-(±)-1-n-propyl-6-phenylhydrazono-7-oxodecahydroquinoline formed in the above reaction.

Alternatively, the above reaction was carried out using a reverse addition procedure: a solution was prepared from 5.5 ml of ethyl formate, 3.3 g of trans-(±)-1-n-propyl-7-oxodecahydroquinoline and 20 ml THF. This solution was added to a solution of 3.8 g of potassium t-tutoxide in 80 ml of THF. The reaction mixture was stirred for 2 hours at about 0° C. at which time TLC indicated that all the starting ketone had reacted. The pH was adjusted to about 6 by the addition of 10% hydrochloric acid. A solution of 7.2 g of sodium acetate in 20 ml of water was added. Next, a phenyldiazonium chloride solution was prepared as above from 1.6 g aniline. The solution of the trans-(±)-1-n-propyl-6-formyl-7-oxo-decahydroquinoline was cannulated rapidly under positive $N_2$ pressure beneath the surface of the phenyldiazonium chloride solution held at 0° C. The reaction mixture was stirred at that temperature for 2 hours and then worked up as above. Flash chromatography yielded 43.5% of the desired trans-(±)-1-n-propyl-6-phenylhydrazono-7-oxodecahydroquinoline (compared with 31.4% by normal addition).

This product was hydrogenated catalytically over 5% Pd/C in ethanol/hydrochloric acid. The hydrogenation mixture was filtered and the filtrate concentrated to reduced to yield crude trans-(±)-1-n-propyl-6-amino-7-oxodecahydroquinoline as the dihydrochloride salt; yield=10.34 g. of a green foam.

Two g. of crude trans-(±)-1-n-propyl-6-amino-7-oxodecahydroquinoline dihydrochloride prepared as above were suspended in a mixture of 50 ml. of THF and 10 ml. of acetic anhydride. The reaction mixture was cooled to about 0° C. Ten ml. of triethylamine were then added. The solid dissolved immediately. The resulting solution was stirred overnight at ambient temperature. The reaction mixture was then poured into water, and the aqueous mixture made strongly basic by the addition of 15N aqueous ammonium hydroxide. The alkaline aqueous mixture was extracted several times with equal volumes of methylene dichloride. The organic layers were combined; the combined layers washed with brine and then dried. Evaporation of the volatile constituents yielded a dark brown residue. The residue was dissolved in THF containing a trace of ammonium hydroxide and the solution flash chromatographed over silica with THF to which a trace of ammonium hydroxide had been added. Fractions shown by TLC (THF plus a trace of ammonium hydroxide) to contain the desired product were combined, and the solvent evaporated therefrom to give 0.65 g. of a yellow waxy solid comprising trans-(±)-1-n-propyl-6-acetylamino-7-oxodecahydroquinoline formed in the above reaction.

A solution of 0.58 g of the acetyl amino compound in 25 ml. of phosphorous oxychloride was heated to reflux temperature for about 4 hours. The reaction mixture then allowed to stand over the weekend at ambient temperature. The solvent was removed in vacuo and the resulting residue dissolved in water. The water solution was made basic with 15N aqueous ammonium hydroxide. The aqueous layer was extracted several times with equal volumes of methylene dichloride. The methylene dichloride extracts were combined, the combined extracts washed with brine and then dried. Evaporation of the solvent yielded a dark viscous residue which was dissolved in THF containing a trace of ammonium hydroxide and the solution flash chromatographed over a flash silica using the same solvent as eluant. Fractions shown by TLC (THF plus a trace of ammonium hydroxide) to contain the desired material were combined and the solvent evaporated therefrom to give 0.48 g. a straw colored oil (89.2% yield). This oil was dissolved in a small amount of methanol to which was added an equivalent of para-toluene sulfonic acid. The solution was heated to boiling and ethyl acetate added. Boiling was continued until crystallization began. The solid which formed was separated by filtration, and recrystallized from a methanol/ether solvent mixture. trans-(±)-2-Methyl-5-n-propyl-4,4a,5,6,7,8-,8a,9-octahydro-oxazolo[4,5-g]quinoline formed in the above reaction melted at 198°–200° C.; yield=0.38 g.

Analysis calculated: C, 62.04; H, 7.44; N, 6.89; Found: C, 61.82; H, 7.24; N, 6.78.

EXAMPLE 3

Preparation of trans-(±)-5-n-propyl-4,4a,5,6,7,8,8a,9-octahydro-oxazolo[4,5-g]quinoline Following the procedure of Example 2, 3.0 g. of trans-(±)-1-n-propyl-6-amino-7-oxodecahydroquinoline dihydrochloride was suspended in 25 ml. of dry THF, the mixture cooled and 6 ml. of a formic acetic mixed anhydride added, followed by the dropwise addition of 5 ml. of triethylamine. The acylation mixture was stirred for 1 hour at room temperature, and was then poured into water. The aqueous mixture was made acidic with 10% hydrochloric acid. The resulting acidic aqueous layer was extracted with ether, and the ether extract discarded. The acidic layer was then made basic by the addition of 15N aqueous ammonium hydroxide, and the now alkaline layer extracted several times with equal volumes of methylene dichloride. The methylene dichloride extracts were combined, the combined extracts washed with brine and then dried. Evaporation of the solvent gave 1.9 g. of viscous yellow oil. The oil was dissolved in THF and the solution flash chromatographed over silica using THF containing a trace of ammonium hydroxide as the eluant. Fractions shown by TLC (using the same eluant) to contain the desired trans-(±)-1-n-propyl-6-formylamino-7-oxodecahydroquinoline were combined and the solvent evaporated therefrom to give 1.0 g. a yellow transparent viscous residue (83.9% yield). The residue crystallized while standing.

A solution was prepared by dissolving 0.63 g. of trans-(±)-1-n-propyl-6-formylamino-7-oxodecahydroquinoline in 8.8 ml. of methanesulfonic acid. The mixture was heated to about 100° C. after which time 1.26 g. of phosphorous pentoxide were added. This new reaction mixture was stirred for 2.5 hours at 100° C., after which time was poured over ice. The acidic solution was made basic by the addition of 15% aqueous sodium hydroxide. The basic mixture was extracted several times with equal volumes of methylene dichloride. The methylene dichloride extracts were combined and dried. Evaporation of the solvent yielded a viscous brown transparent oil which was dissolved in THF and flash chromatographed over silica. The column was eluted with THF containing a trace of ammonium hydroxide. The second fraction consisted of 0.26 g. of a viscous brown transparent oil comprising trans-(±)-5-n-propyl-4,4a,5,6,7,8,8a,9-octahydro-oxazolo[4,5-g]quinoline formed in the above reaction. The compound was converted to the maleate salt in ethanol. The salt was recrystallized from an ether/ethanol solvent mixture; yield=0.26 g. of gold crystals melting at 158°–160° C.

Mass spectrum, molecular ion at 220.

Elemental analysis: Calc.: C, 60.78; H, 7.19; N, 8.33; Found: C, 60.94; H, 7.26; N, 8.20.

EXAMPLE 4

Preparation of trans-(±)-2-Oxo-5-n-propyl-4,4a,5,6,7,8,8a,9-octahydro-oxazolo[4,5-g]quinoline Following the procedure of Example 2, 5 g. of trans-(±)-1-n-propyl-6-amino-7-oxodecahydroquinoline dihydrochloride were suspended in 50 ml. of THF. The suspension was cooled to about 0° C. Ten ml. of methylchloroformate were added, followed by the dropwise addition of 10 ml of triethylamine. The reaction mixture was stirred for 2 hours at room temperature, at the end of which time it was diluted with an excess of 1N hydrochloric acid. The acidic layer was extracted once with ether, and the ether extract discarded. The acidic layer was then cooled by pouring over ice, and the resulting cooled mixture made strongly basic with 15N aqueous ammonium hydroxide. The alkaline mixture was now extracted several times with equal volumes of methylene dichloride. The methylene dichloride extracts were combined and dried. The evaporation of the solvent yielded a dark yellow, viscous residue which was dissolved in 1:1 THF/hexane containing a trace of ammonium hydroxide. The solution was flash chromatographed over silica using the same solvent as the eluant. Fractions shown by TLC (using the same solvent system) to contain the desired trans-(±)-1-n-propyl-6-methoxycarbonylamino-7-oxodecahydroquinoline were combined and the solvent evaporated therefrom yield 1.47 g. (67% yield) of a viscous yellow residue having a molecular ion by mass spectroscopy at 268.

A solution was prepared from 0.4 g. of the above carbamate in 10 ml. of oleum. The acidic mixture was stirred for 18 hours at room temperature and then poured over ice. The aqueous acidic layer was then made basic by the addition of 15N aqueous ammonium hydroxide. The now alkaline layer was extracted several times with equal volumes of methylene dichloride. The methylene dichloride extracts were combined, and the combined extracts washed with brine and then dried. Evaporation of the solvent yielded a dark viscous residue. The residue was dissolved in 1:2 THF/hexane containing a trace of ammonium hydroxide and the solution flash chromatographed over silica. Fractions shown by TLC (1:1 THF/hexane plus a trace of ammonium hydroxide) to contain trans-(±)-2-methoxy-5-n-propyl-4,4a,5,6,7,8,8a,9-octahydrooxazolo[4,5-g]quinoline were combined and the solvent removed therefrom to yield 0.1 g. of a viscous, yellow residue. The residue was dissolved in ether, and the ethereal solution saturated with gaseous hydrogen chloride. The resulting salt was crystallized from an ethanol/ether solvent mixture, during which procedure the 2-methoxy group hydrolysed to yield the corresponding 2-oxazolone. 0.07 g. of trans-(±)-2-oxo-5-n-propyl-4,4a,5,6,7,8,8a,9-octahydro-oxazolo[4,5-g]quinoline, as the hydrochloride salt were recovered, melting above 250° C.; molecular ion at 236 by mass spectroscopy.

Analysis calc.: C, 57.24; H, 7.76; N, 10.27; Found: C, 57.28; H, 7.75; N, 10.20.

Trans-(±)-2-oxo-5-n-propyl-4,4a,5,6,7,8,8a,9-octahydro-1H-oxazolo[4,5-g]quinoline thus prepared can be reacted with phosphorous pentachloride or phosphorous oxychloride or PBr$_3$ to yield the corresponding chloro or bromo derivative, trans-(±)-2-chloro-5-n-propyl-4,4a,5,6,7,8,8a,9-octa hydro-oxazolo[4,5-g]quinoline or trans-(±)-2-bromo-5-n-propyl-4,4a,5,6,7,8,8a,9-octahydro-oxazolo[4,5-g]quinoline. This compound can in turn be reacted with secondary or primary amines with ammonia or with cyclic amines such as piperidine, pyrrolidine or morpholine to yield the corresponding 2-amino or substituted amino octahydro-oxazolo[4,5-g]quinoline.

EXAMPLE 5

Preparation of trans-(±)-2-Dimethylamino-5-n-propyl-4,4a,5,6,7,8,8a,9-octahydro-oxazolo[4,5-g]quinoline A solution was prepared by dissolving 0.99 g of trans-(±)-1-n-propyl-6-methoxycarbonylamino-7-oxodecahydroquinoline (from Example 4) in 20 ml of oleum and the solution stirred at room temperature for about 20 hours. The acidic mixture was then poured over ice and this diluted acidic solution was stirred at room temperatue for 0.5 hr. The solution was then made basic by the addition of an excess of 14N aqueous ammonium hydroxide. The aqueous alkaline mixture was extracted several times with equal volumes of a 3:1 chloroform/isopropanol solvent mixture. The organic layers were combined, and the combined layers washed with brine and then dried. Evaporation of the solvent gave an amber viscous residue which was flash chromatographed over silica with THF containing a trace of NH$_4$OH. Fractions shown by TLC to contain the desired 2-methoxy derivatives were combined and the solvent removed to yield 0.42 g of an oily residue comprising trans-(±)-2-methoxy-5-n-propyl-4,4a,5,6,7,8,8a,9-octahydro-oxazolo[4,5-g]quinoline. NMR was consistent with proposed structure. A reaction mixture was prepared by placing 0.15 g of this product and 10 ml of dimethylamine in a sealed tube and heating the sealed tube to 100° C. for one hour. The excess dimethylamine was removed by evaporation leaving a viscous brown residue. The residue was flash chromatographed over silica using 1:1 THF/hexane with a trace of NH$_4$OH as the eluant. Fractions shown by TLC (same solvent system) to contain the desired material were combined and the solvent removed to yield 50 mg of a pale yellow transparent glass comprising trans-(±)-2-dimethylamino-5-n-propyl-4,4a,5,6,7,8,8a,9-octahydro-oxazolo[4,5-g]quinoline formed in the above reaction.

NMR was consistent with the proposed structure (sharp singlet at δ2.9 integrating for 6 protons).

EXAMPLE 6

Alternate Preparation of Trans-(±)-1-n-propyl-7-oxodecahydroquinoline

A solution was prepared by dissolving 9.9 g of lithium in 2 l of anhydrous liquid ammonia. 98.7 g of 4-(3-n-propylamino)propylanisole were dissolved in a mixture of 27.8 ml of anhydrous ethanol and 300 ml of THF. This solution was added slowly in dropwise fashion with stirring to the lithium in liquid ammonia solution. After the addition had been completed. The reaction mixture was stirred for about 45 minutes. Water was then added slowly until the blue color of dissolved Li had been discharged. A stream of $N_2$ was passed over the reaction mixture overnight to evaporate the ammonia. Additional water was then added to dissolve the salts which had formed. The alkaline aqueous solution was extracted three times with equal volumes of diethyl ether. The ethereal extracts were combined and dried. Evaporation of the ether yielded 93.2 g of 1-methoxy-4-(3-n-propylamino)propyl-1,4-cyclohexadiene; yield=93.5%.

One-tenth gram of the above compound was stirred at ambient temperature for one hour with 15 ml 0.1N hydrochloric acid. The reaction mixture was made basic with 15N aqueous $NH_4OH$ and the alkaline mixture extracted several times with equal volumes of $CH_2Cl_2$. The organic layers were combined and dried. The solvent was evaporated to dryness in vacuo.

TLC and NMR of the residue indicated the presence of 4-(3-n-propylaminopropyl)cyclohex-3-enone plus a small amount of cis-(±)-1-n-propyl-7-oxodecahydroquinoline produced by spontaneous cyclization of the $\Delta^2$ isomer formed during the reaction.

Five grams of crude compound prepared as above were added to a solution of 14.9 millimoles of sodium methylate in 10 ml of methanol. The resulting solution was stirred at ambient temperatures for 18 hours, and was then poured into water. The alkaline layer was extracted several times with equal volumes of $CH_2Cl_2$. The organic extracts were combined and dried, and the solvent removed by evaporation in vacuo to give 4.5 g of a dark red-orange residue. The residue was dissolved in hexane/THF (2:1) containing a trace of $NH_4OH$, and the solution chromatographed over silica, using the same solvent as eluant. Early fractions yielded primarily cis-(±)-1-n-propyl-7-oxodecahydroquinoline. Later fractions were shown to contain trans-(±)-1-n-propyl-7-oxodecahydroquinoline; yield=2.34 g.

PREPARATION 1

Ten g. of (−)-di-p-toluoyltartaric acid were dissolved in 75 ml. of warm methanol. The solution was added to a solution of 5.05 g. of trans-dl-1-n-propyl-6-oxodecahydroquinoline in 15 ml. of methanol. The reaction mixture was brought to a boil and was then allowed to cool to ambient temperature. After remaining at ambient temperature overnight, crystallization was induced by the addition of seed crystals previously obtained. The crystalline tartarate salt was isolated by filtration and the filter cake washed with methanol; yield=2.813 g. (18.7%) of a white crystalline solid comprising the (−)-di-p-toluoyltartrate of 4aR,8aR-1-n-propyl-6-oxodecahydroquinoline; $[\alpha]_D^{25°} = -107.49°$ (MeOH, c=1). Recrystallization of the salt from methanol gave 1.943 g. of the optically pure salt, $[\alpha]_D^{25°} = -108.29°$ (MeOH, c=1). The (−)-di-p-toluoyltartrate salt thus obtained was treated with dilute aqueous sodium hydroxide and the resulting alkaline solution extracted with methylene dichloride. The methylene dichloride extract was dried and concentrated, and the solvent removed therefrom in vacuo. The resulting residue was distilled to yield a colorless oil comprising purified 4aR,8aR-1-n-propyl-6-oxodecahydroquinoline; $[\alpha]_D^{25°} = -88.51°$ (MeOH, c=1).

The 4aS,8aS derivative can be prepared in similar fashion by reacting (+)-di-p-toluoyltartaric acid with the racemate.

The corresponding 4aR,8aR-1-methyl, 1-ethyl or 1-allyl derivatives can be prepared similarly from the trans-(±)-1-methyl, 1-ethyl or 1-allyl racemate.

The preparation of pharmaceutically-acceptable acid addition salts of the compounds of this invention, particularly the hydrohalide salts, is illustrated in the above examples. Generally speaking, a solution of an equivalent of the free base represented by I, III or IIIa in a lower alkanol is mixed with an equivalent of the acid, also in solution in a lower alkanol. The salt is recovered by evaporation of the solvent and purified by recrystallization. Alternatively, an equivalent of the free base in a nonpolar organic solvent such as ether can be mixed with an equivalent of the acid, also in ether. In this procedure, the salt is usually insoluble in the solvent system and is recovered by filtration.

The compounds represented by I, III or IIIa have at least two basic amine groups, the more basic group being the octahydroquinoline ring nitrogen. Disalts can be formed with these compounds by using at least two equivalents of acid per equivalent of base. In general, only the stronger organic and inorganic acids will form disalts; i.e. the mineral acids, toluenesulfonic acid, methanesulfonic acid etc. Dihydrochloride salts are conveniently prepared by dissolving the free base in ether, saturating the ethereal solution with gaseous HCl, and recovering the dihydrochloride salt by filtration.

As previously stated, the drugs of this invention as represented by formulas I and III above are D-2 dopamine agonists. One of such D-2 -dopamine agonist activities is the inhibition of prolactin secretion, as demonstrated by the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug. The purpose of the reserpine was to keep the rat prolactin levels uniformly elevated. The compound was dissolved in 10 percent ethanol, and injected intraperitoneally at doses of 0.017, 0.03, 0.17 and 0.3 μmoles/kg. The compound was administered at each dose level to a group of 10 rats, and a control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats, gives the percent inhibition of prolactin secretion attributable to the given dose.

The compounds represented by I and III are also active by the oral route, but at higher doses.

Compounds according to I and III, dopamine D-2 agonists, have also been found to affect turning behavior in 6-hydroxydopamine-lesioned rats in a test procedure designed to uncover compounds useful for the treatment of Parkinsonism. In this test, nigroneostriatal-lesioned rats are employed, as prepared by the procedure of Ungerstedt and Arbuthnott, *Brain Res,* 24, 485 (1970). A compound having dopamine agonist activity causes the rats to turn in circles contralateral to the side of the lesion. After a latency period, which varies from compound to compound, the number of turns is counted over a 15-minute period.

The compounds of this invention I, and III are effective in the treatment of hypertension. The compounds demonstrated such activity in a standard laboratory test; ie., upon administration to SHR (spontaneously hypertensive rats) as follows:

Adult male spontaneously hypertensive rats (SHR) (Taconic Farms, Germantown, N.Y.), weighing approximately 300 g. were anesthetized with pentobarbital sodium (60 mg./kg., i.p.). The trachea was cannulated and SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation.

Table 1 below gives the results of these determinations. In the table, column 1 gives the name of the drug, column 2 dose in μg/kg, column 3 percent change in mean arterial blood pressure plus or minus standard error and column 4, percent change in heart rate plus or minus standard error. Four rats were used at each dose level.

TABLE 1

| Name of drug | dose μg/kg | % change in BP | % change in heart rate |
|---|---|---|---|
| trans-(±)-2-amino-5-n- | 0.1 | −18.3 ± 5.7 | −8.5 ± 2.2 |
| propyl-4,4a,5,6,7,8,8a,9- | 1 | −8.6 ± 1.6 | −4.4 ± 0.9 |
| octahydro-oxazolo[4,5-g]- | 10 | −15.1 ± 1.1 | −5.6 ± 0.7 |
| quinoline dihydrochloride | 100 | −39.0 ± 1.9* | −17.5 ± 2.3 |
|  | 100 | −51.2 ± 1.2* | −19.1 ± 3.4 |
| baseline: mean arterial BP = 187 ± 10 mm Hg; | | | |
| mean heart rate = 336 ± 13 beats/min. | | | |
| trans-(±)-2-methyl-5-n- | 1 | −3.2 ± 0.5 | −2.4 ± 0.8 |
| propyl-4,4a,5,6,7,8,8a,9- | 10 | −7.0 ± 1.0 | −2.8 ± 0.4 |
| octahydro-oxazolo[4,5-g]- | 100 | −19.6 ± 1.4* | −16.1 ± 7.6 |
| quinoline p-tosylate | 1000 | −26.2 ± 4.3* | −23.6 ± 4.4 |
| baseline: mean arterial BP = 212 ± 4 mm Hg; | | | |
| mean heart rate = 381 ± 19 beats/min. | | | |
| trans-(±)-5-n-propyl- | 1 | −5.0 ± 1.2 | −3.6 ± 0.5 |
| 4,4a,5,6,7,8,8a,9-octa- | 10 | −10.2 ± 1.0 | −4.6 ± 0.6 |
| hydro-oxazolo[4,5-g]0 | 100 | −27.4 ± 20* | −28.5 ± 2.6 |
| quinoline maleate | 1000 | −37.7 ± 4.9* | −31.8 ± 3.7 |
| baseline: mean arterial BP = 194 ± 5 mm Hg; | | | |
| mean heart rate = 371 beats/min. | | | |

*Duration of 15 min or greater

The same three compounds from Table 1 exhibit selective affinity for apomorphine binding sites (as measured by inhibition of $^3$H-apomorphine binding). With trans-(±)-2-methyl-5-n-propyl-4,4a,5,6,7,8,8a,9-octahydrooxazolo[4,5-g]quinoline; the ratio of binding, to apomorphine sites vs spiperone sites is 40 to 1.

Activity in affecting sexual behavior by the compounds according to I or III where R is allyl, methyl, ethyl or n-propyl or $R^1$ is $R^3$ is demonstrated by measuring mount latency, intromission latency, ejaculatory latency, postejaculatory interval, mount frequency and intromission frequency in male rats who require at least five minutes to achieve ejaculation when a sexually receptive female is introduced into the behavioral arena prior to drug treatment. Reduction in one or more of the above indice indicates a positive effect on sexual behaviour in male mammals including, but not limited to, improving potency. Sexually unresponsive male rats can also be used in such tests. Positive effects upon the sexual behaviour of female mammals are found when drugs according to I or III are administered to ovariectomized, estrogen-treated rats, and the lordosis-to-mount ratio measured. An increase indicates a positive effect to be expected in female mammals suffering from a sexual dysfunction.

The compounds of this invention are usually administered for therapeutic purposes in a variety of oral formulations as illustrated below.

Hard gelatin capsules are prepared using the following ingredients:

| | Quantity (mg./capsule) |
|---|---|
| Active compound | .1–2 mg |
| Starch dried | 200 |
| Magnesium stearate | 10 |

The above ingredients are mixed and filled into hard gelatin capsules.

A tablet formulation is prepared using the ingredients below:

| | Quantity (mg./tablet) |
|---|---|
| Active compound | .1–2 mg |
| Cellulose, microcrystalline | 400 |
| Silicon dioxide, fumed | 10 |
| Stearic acid | 5 |

The components are blended and compressed to form tablets.

Alternatively, tablets each containing 0.1–2 mg. of active ingredient are made up as follows:
Active ingredient: 0.1–2 mg.
Starch: 45 mg.
Microcrystalline cellulose: 35 mg.
Polyvinylpyrrolidone (as 10% solution in water): 4 mg.
Sodium carboxymethyl starch: 4.5 mg.
Magnesium stearate: 0.5 mg.
Talc: 1 mg.

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed with a tablet machine to yield tablets.

Capsules each containing 0.1-2 mg. of medicament are made as follows:
Active ingredient: 0.1-2 mg.
Starch: 59 mg.
Microcrystalline cellulose: 59 mg.
Magnesium stearate: 2 mg.

The active ingredient, cellulose, starch and magnesium stearate are blended, passed through a No. 45 mesh U.S. sieve, and filled into hard gelatin capsules.

Suspensions each containing 0.1-2 mg. of medicament per 5 ml. dose are made as follows:
Active ingredient: 0.1-2 mg.
Sodium carboxymethyl cellulose: 50 mg.
Syrup: 1.25 ml.
Benzoic acid solution: 0.10 ml.
Flavor: q.v.
Color: q.v.
Purified water to: 5 ml.

The medicament is passed through a No. 45 mesh U.S. sieve and mixed with the sodium carboxymethylcellulose and syrup to form a smooth paste. The benzoic acid solution, flavor and color are diluted with some of the water and added with stirring. Sufficient water is then added to produce the required volume.

For oral administration in treating sexual dysfunction, improving potency, lowering blood pressure (either thru a D-2 or D-1 mechanism), for increasing renal vascular flow, treating depression or anxiety, alleviating the symptoms of Parkinsonism or inhibiting prolactin release, tablets, capsules or suspensions containing from about 0.1 to about 2 mg. of active drug per dose are given 3-4 times a day, giving a daily dosage of 0.3 to 8 mgs. or, for a 75 kg. person, about 2.25 to about 600 mg./day. The intravenous dose is in the range from about 0.1 to about 100 mcg./kg.

We claim:

1. A trans-($\pm$)-racemate containing trans-($-$) and trans-($+$) enantiomers of the formulas

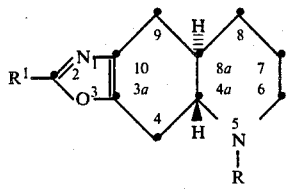

and

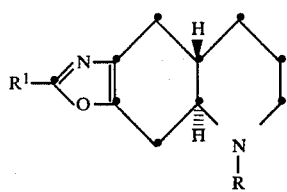

wherein R is $C_{1-3}$ straight-chain alkyl or allyl and $R^1$ is H, $C_{1-3}$ alkyl, O—$C_{1-3}$ alkyl, $NH_2$, $NHC_{1-3}$ alkyl, $N(C_{1-3}$ alkyl$)_2$, 1-pyrrolidinyl, 1-piperidinyl or $NHCOC_{1-3}$ alkyl; and pharmaceutically-acceptable acid addition salts thereof.

2. A trans-($-$)-4aR,8aR enantiomer or a salt thereof according to claim 1.

3. A racemate according to claim 1 in which R is n-propyl.

4. A 4aR,8aR-enantiomer according to claim 2 in which R is n-propyl.

5. A racemate according to claim 1 in which R is $C_{1-3}$ straight-chain alkyl or allyl and $R^1$ is $NH_2$, $C_{1-3}$ alkyl, $NHC_{1-3}$ alkyl, $N(C_{1-3}$ alkyl$)_2$, $NHCOC_{1-3}$ alkyl, 1-pyrrolidinyl or H, or an acid addition salt thereof formed with a pharmaceutically-acceptable acid.

6. A 4aR,8aR enantiomer according to claim 2 in which R is $C_{1-3}$ straight-chain alkyl or allyl and $R^1$ is $NH_2$, $NHC_{1-3}$ alkyl, $N(C_{1-3}$ alkyl$)_2$, $NHCOC_{1-3}$ alkyl, 1-pyrrolidinyl, 1-piperidinyl, $C_{1-3}$ alkyl, OH or H, or a pharmaceutically-acceptable acid addition salt thereof.

7. A racemate according to claim 5 in which $R^1$ is $NH_2$.

8. A 4aR,8aR enantiomer according to claim 6 in which $R^1$ is $NH_2$.

9. A hydrohalide salt of a racemate according to claim 1.

10. A hydrohalide salt of a 4aR,8aR enantiomer according to claim 2.

11. A racemate according to claim 1 in which R is H.

12. A 4aR,8aR enantiomer according to claim 2 in which R is H.

13. A racemate according to claim 1, said racemate being trans-($\pm$)-2-amino-5-n-propyl-4,4a,5,6,7,8,8a,9-octahydro-oxazolo[4,5-g]quinoline.

14. A racemate according to claim 1, said racemate being trans-($\pm$)-5-n-propyl-4,4a,5,6,7,8,8a,9-octahydro-oxazolo[4,5-g]quinoline.

15. A racemate according to claim 1, said racemate being trans-($\pm$)-2-methyl-5-n-propyl-4,4a,5,6,7,8,8a,9-octahydro-oxazolo[4,5-g]quinoline.

16. A dihydrohalide salt of the racemate of claim 13.

17. A method of inhibiting the secretion of prolactin in a mammal which consists of administering to a mammal having a physiologic condition characterized in part by elevated prolactin levels an amount of a racemic drug according to claim 6 effective to reduce prolactin secretion.

18. A method of treating hypertension in mammals which consist of administering to a hypertensive mammal a blood-pressure lowering dose of a racemate according to claim 5.

19. A method of treating depression in mammals which consists of administering to a mammal in a depressed state, a depression alleviating dose of a racemate according to claim 5.

20. A method of treating anxiety in mammals which consist of administering to an anxious mammal an anxiety relieving dose of a racemate according to claim 5.

21. A method for potentiating sexual behavior in mammals in need of such potentiation which comprises administering to said mammals an effective dose of a trans-($\pm$)-racemate of claim 5.

22. A method for treating sexual dysfunction in mammals suffering from such dysfunction and in need of treatment which comprises administering to said mammals an effective dose of a trans-($\pm$)-racemate of claim 5.

23. A method of restoring potency in impotent male mammals in need of treatment which comprises administering to such impotent male mammals a potency restoring dose of a trans-($\pm$)-racemate of claim 5.

24. A method of treating Parkinson's Syndrome consisting of administration to a mammal suffering from Parkinson's Syndrome and in need of treatment an effective dose of a 4aR,8aR enantiomeric drug according to claim 6.

25. A method of inhibiting the secretion of prolactin in a mammal which consists of administering to a mammal having a physiologic condition characterized in part by elevated prolactin levels, an amount of a 4aR,-8aR enantiomeric drug according to claim 6 effective to reduce prolactin secretion.

26. A method of treating hypertension in mammals which consist of administering to a hypertensive mammal a blood-pressure lowering dose of a 4aR,8aR enantiomer according to claim 6.

27. A method of treating depression in mammals which consists of administering to a mammal in a depressed state, a depression alleviating dose of a 4aR,8aR enantiomer according to claim 6.

28. A method of treating anxiety in mammals which consist of administering to an anxious mammal an anxiety relieving dose of a 4aR,8aR enantiomer according to claim 6.

29. A method for potentiating sexual behavior in mammals in need of such potentiation which comprises administering to said mammals an effective dose of a 4aR,8aR enantiomer of claim 6.

30. A method for treating sexual dysfunction in mammals suffering from such dysfunction and in need of treatment which comprises administering to said mammals an effective dose of a 4aR,8aR enantiomer of claim 6.

31. A method of restoring potency in impotent male mammals in need of treatment which comprises administering to such impotent male mammals a potency restoring dose of a 4aR,8aR enantiomer of claim 6.

32. A pharmaceutical formulation in unit dosage form adapted for administration to counter depression, alleviate anxiety, reduce elevated blood pressure, lower excessively high prolactin levels, treat Parkinson's Syndrome, potentiate sexual behaviour, treat sexual dysfunction or restore sexual potency comprising per dosage unit, a standard pharmaceutical excipient plus an amount of a drug according to claim 5 to inhibit the secretion of prolactin, to relieve anxiety, to counter depression, to lower blood pressure of hypertensives, to treat Parkinson's Syndrome, to potentiate sexual behaviour, to treat sexual dysfunction or to restore sexual potency.

33. A pharmaceutical formulation in unit dosage form adapted for administration to counter depression, alleviate anxiety, reduce elevated blood pressure, lower excessively high prolactin levels, treat Parkinson's Syndrome, potentiate sexual behaviour, treat sexual dysfunction or restore sexual potency comprising per dosage unit, a standard pharmaceutical excipient plus an amount of a drug according to claim 6 to inhibit the secretion of prolactin, to relieve anxiety, to counter depression, to lower blood pressure of hypertensives to treat Parkinson's Syndrome, to potentiate sexual behaviour, to treat sexual dysfunction or to restore sexual potency.

34. A formulation according to claim 33 in which trans-($\pm$)-2-amino-5-n-propyl-4,4a, 5,6,7,8,8a,9-octahydro-oxazolo[4,5-g]quinoline or a pharmaceutically-acceptable acid addition salt thereof is the active D-2 agonist.

35. A racemate of the formula

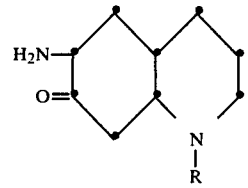

wherein R is $C_{1-3}$ straight chain alkyl, allyl, benzyl or H, and acid addition salts thereof.

36. A 4aR,8aR enantiomer of the formula

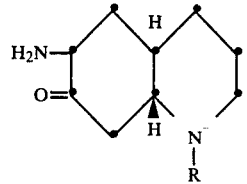

wherein R is $C_{1-3}$ straight chain alkyl, allyl, benzyl or H, and acid addition salts thereof.

37. A trans-($\pm$)-racemate containing trans-(−) and trans-(+) enantiomers of the formulas

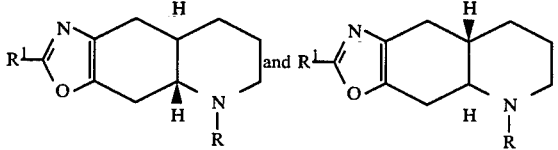

wherein R is H or benzyl, and $R^1$ is Cl, Br, or OH.

* * * * *

UNITED STATES PATENT AND TRADEMARK OFFICE
CERTIFICATE OF CORRECTION

PATENT NO. : 4,698,347

DATED : October 6, 1987

INVENTOR(S) : John M. Schaus et al.

It is certified that error appears in the above-identified patent and that said Letters Patent is hereby corrected as shown below:

Column 1, line 1, in the title "OCTAHYDRO-OXAZOLO[4,5-G]QUINOLINES" should read --OCTAHYDRO-OXAZOLO[4,5-G]QUINOLINE--.

Column 24, lines 27-35, in Claim 36, the formula which reads

" 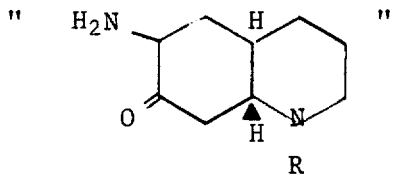 "  should read

-- 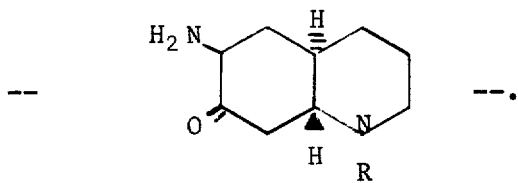 --.

UNITED STATES PATENT AND TRADEMARK OFFICE
CERTIFICATE OF CORRECTION

PATENT NO. : 4,698,347

DATED : October 6, 1987

INVENTOR(S) : John M. Schaus et al.

It is certified that error appears in the above—identified patent and that said Letters Patent is hereby corrected as shown below:

Column 24, lines 40-48, in Claim 37, the formulas which read

" 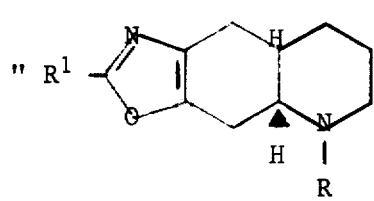 and 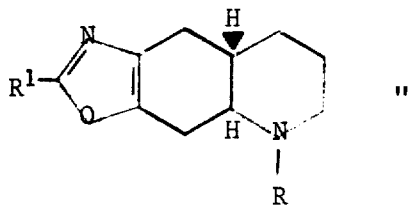 "

should read

-- 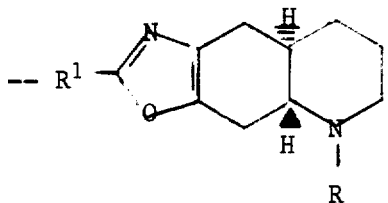 and 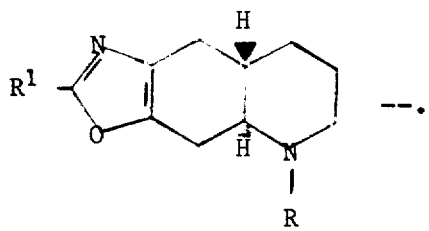 --.

Signed and Sealed this

Twentieth Day of September, 1988

Attest:

DONALD J. QUIGG

Attesting Officer

Commissioner of Patents and Trademarks